United States Patent [19]

Itzhak

[11] Patent Number: 5,441,982
[45] Date of Patent: Aug. 15, 1995

[54] THERAPEUTICS FOR MANAGEMENT OF COCAINE INDUCED TOXICITY

[76] Inventor: Yossef Itzhak, 9407 SW. 151st Ave., Miami, Fla. 33196

[21] Appl. No.: 125,808

[22] Filed: Sep. 24, 1993

[51] Int. Cl.⁶ .................. A61K 31/22; A61K 31/195
[52] U.S. Cl. ........................................ 514/55; 514/565; 514/554; 514/406; 514/646; 514/812
[58] Field of Search ............... 514/551, 554, 565, 406, 514/812, 646

[56] References Cited

U.S. PATENT DOCUMENTS 5,225,440 7/1993 London et al. ................. 514/535

OTHER PUBLICATIONS

Journal of Pharmacology texperimental Therapeutics v. 262 *2, pp. 464–470 Itzhakttstein, 1992 "Sensit.to toxic effects of cocaine in mice . . . ".
1989 Life Sciences v. 45, pp. 599–606, Karla et al, "Blockade of Reverse Tolerance".
1991 European Journal of Pharm. 204 (1991) 339-340 Nowicki et al., "Nitric Oxide . . .".
Pudiak et al., "L–Name and MK–801 Attenuate Sensitization . . . ", Life Sciences, vol. 53, pp. 1571–1524 (1993).
Embase Abstract 93324192, Kimes et al., Psychopharmacology 112/4, pp. 521–524 (1993).
Embase Abstract 93242193, Thorat et al., Brian Research, 621/1, pp. 171–174 (1993).
Chemical Abstracts 117(25):245479a, Kolesnikov et al., Eur. J. Pharmacol., 221 (2–3), pp. 399–400 (1992).

*Primary Examiner*—Marianne M. Cintins
*Assistant Examiner*—M. Moezie
*Attorney, Agent, or Firm*—Alvin S. Blum

[57] ABSTRACT

Repetitive administrations of cocaine over a period of days causes the animal body to become more sensitive to the drug. A dose of cocaine that was not toxic to a novice user may be toxic or even lethal to an habituated user. These toxic effects include craving, seizures, brain ischemia and death. The mechanism of action of these toxic effects appears to be through the glutamatergic neurotransmitter system as evidenced by blocking with antagonists for N-methyl-D-aspartate receptors. However, these antagonists have undersirable side effects. Applicant demonstrates that the toxic effects of repetitive cocaine administrations can be reversed by the administration of inhibitors of the enzyme nitric oxide synthase which is also involved in the neurotransmitter system. The drugs which inhibit the enzyme nitric oxide synthase include N-nitro-L-arginine and N-nitro-L-arginine methyl ester. The method of treatment with these drugs includes administration in various forms by various routes.

6 Claims, 1 Drawing Sheet

THERAPEUTICS FOR MANAGEMENT OF COCAINE INDUCED TOXICITY

BACKGROUND OF THE INVENTION

The present invention relates to cocaine induced sensitization and toxicity, and more specifically to the use of nitric oxide synthase inhibitors in the treatment of cocaine induced sensitization and toxicity in humans.

During the last decade cocaine became the major drug of abuse in the U.S. The powerful addicting properties of the drug result in not only psychosocial misery, but also serious pathophysiological complications that are due to repeated use of the drug. Animal models and human studies have documented the development of severe neurological disorders, such as seizures and brain ischemia with irreversible brain damage following repeated exposure to cocaine. Cocaine related death due to the chronic exposure to cocaine is also documented from animal models and clinical studies.

After repeated doses of cocaine, the body becomes more responsive to the drug so that a dose that was not toxic to a novice user may be toxic or even lethal to an habituated user.

Since there is no successful "antidote" or antagonist or cocaine abuse, the development of therapeutics for the management of cocaine induced toxicities and cocaine craving is a major issue in drug abuse treatment. Several recent studies, including Applicant's publication: Itzhak and Stein, J. Pharmacol. Exp. tHER. 262, 464–470 (1992) suggest the involvement of the glutamatergic system in the effects of cocaine. Particularly, antagonists for the N-methyl-D-aspartate (NMDA) type of glutamate receptors block cocaine induced seizures and lethality in mice. However, the use of NMDA receptor antagonists to treat cocaine-induced toxicities, such as seizures and brain ischemia, may be limited because of the serious side effects of the NMDA receptor antagonists. Although they are considered as neuroprotective agents, MNDA-receptor antagonists cause undesirable psychotomimetic effects.

SUMMARY OF THE INVENTION

It is, accordingly, an object of the invention to provide effective means of treatment of cocaine induced sensitization and toxicity that do not have undesirable side effects.

Applicant has discovered that nitric oxide synthase (NOS) inhibitors can completely abolish cocaine induced seizures and death. Progressive increase in the toxic effects of cocaine was shown by following experimental animals after uniform daily doses of cocaine. Convulsions had occured in all animals by the seventh day and only 60% were still alive. However, pretreatment of animals with NOS inhibitors prevented both the convulsions and the deaths. The continued or repetitive use of other addictive drugs such as the opioids, including morphine and its derivatives, produces an opposite effect. The body becomes less responsive to the size dose, until finally, withdrawal of the drug results in serious physiologic reactions.

U.S. Pat. No. 5,225,440 issued Jul. 6, 1993 to London and Kimes discloses the use of nitric oxide synthase inhibitors for the treatment of symptoms due to withdrawal of opioids. This is conceptually the opposite teaching wherein the absence of an addictive drug such as heroin causes symptoms relieved by NOS inhibitors. In contrast, Applicant teaches that the presence of the addictive drug cocaine causes symptoms relieved by NOS inhibitors.

An advantage of the NOS inhibitors is that they have been shown to be without serious side effects when used clinically in the treatment of other disorders such as septic shock.

These and other objects, advantages and features of the invention will become more apparent when the detailed description is studied in conjunction with the accompanying drawings.

DETAILED DESCRIPTION OF PREFERRED EMBODIMENTS OF THE INVENTION

Figure 1:
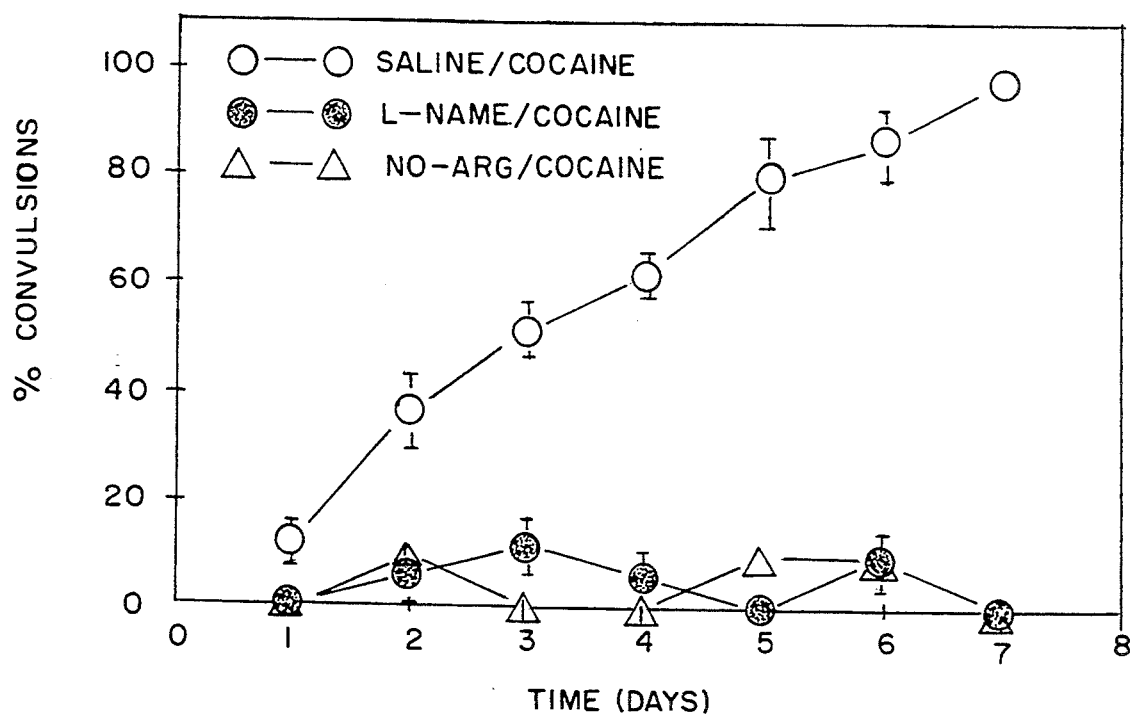
FIG. 1 shows the comparative effects of pretreatment with two different NOS inhibitors on cocaine induced convulsive seizures in mice receiving cocaine repetitively over a seven day period.
Figure 2:
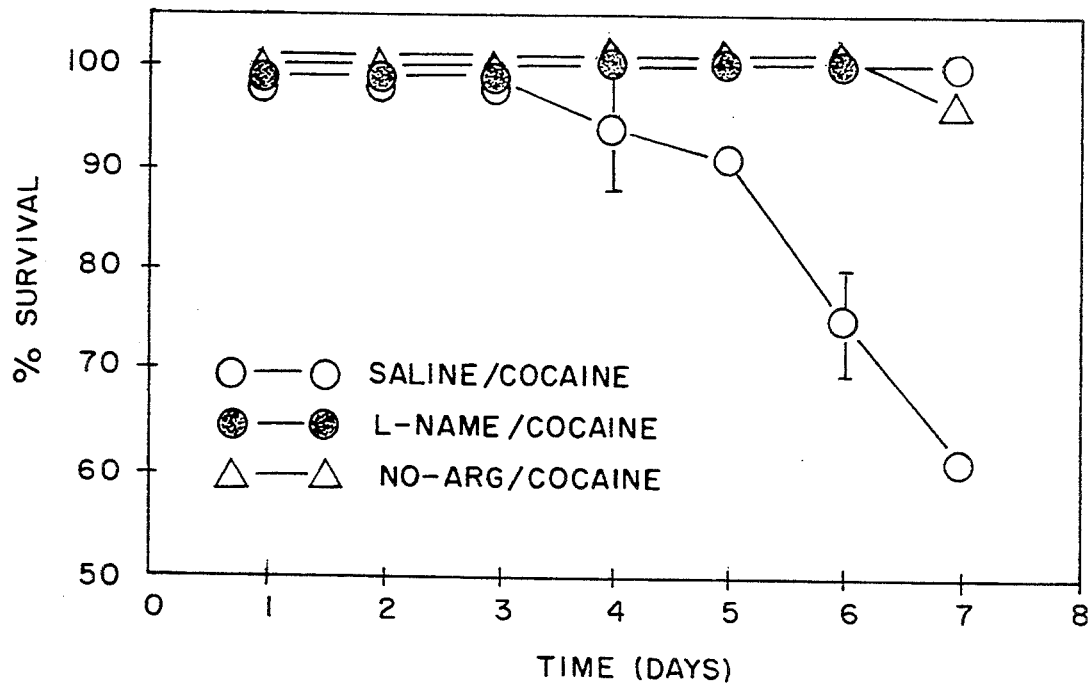
FIG. 2 shows the comparative effects of pretreatment with two different NOS inhibitors on cocaine induced death in mice receiving cocaine over a seven day period.

In the search for safer agents that may be useful in treating cocaine induced toxicity, Applicant has discovered that drugs that block the enzyme nitric oxide (NO) synthase completely abolish cocaine induced seizures and lethality in mice (see TABLE 1). NO synthase inhibitors such as N-nitro-L-arginine methyl ester (L-NAME) and N-nitro-L-arginine (NO-Arg) are known drugs used clinically for the treatment of septic shock. Recent in-vitro studies, and a few in-vivo investigations have demonstrated that these drugs have protective effects against NMDA-receptor mediated neurotoxicity. Thus, it is though that NO, a putative neurotransmitter in the brain, is involved in DA-receptor mediated neurotoxicity. Applicant's recent studies are the first to document that NOS inhibitors have protective effects against cocaine induced toxicity. Results from these studies are presented in TABLE 1. FIG. 1 and FIG. 2. Briefly, Swiss-Webster mice were pretreated with either saline, L-NAME (100 mg/kg/day) or NO-Arg (25 mg/kg/day) 60 min before the administration of cocaine (45 mg/kg/day) for 7 days. The progressive increase in the adverse and toxic effects of repetitive cocaine was manifested by an increase in the convulsive and lethal responses to cocaine. Following the 7th day of saline/cocaine treatment only 60% of the animals survived, and 100% of the animals seized. However, the pretreatment with either L-NAME or NO-Arg completely protected against both the development of convulsions and the lethal effects of cocaine (FIG. 1 and FIG. 2 ).

That the protective effects of these two NO synthase inhibitors is not mediated via a direct interaction of the drugs with the NMDA receptor complex is manifested by the finding that the drugs do not inhibit the binding of ligands that interact with the NMDA receptors complex. Data presented in TABLE 2, indicate that even at the high concentration of 100 uM NO synthase inhibitors do not affect the binding of tritium labeled CGP 39653 to the NMDA receptor, neither do they affect the binding of tritium labeled MK-801 to PCP receptor localized in the ionophore of the NDA receptor complex. These findings suggest that the protective effects of the NO synthase inhibitors against cocaine induced toxicity is mediated via the inhibition of NO synthase.

The advantage of these drugs over the NMDA receptor antagonists is first that they have been tested clinically for the treatment of septic shock, and second, Applicant's studies demonstrate that no apparent behavioral and toxic effects, such as loss in body weight and lethality developed in the animals administered with NO synthase inhibitors alone.

In summary, the data indicates that NOS inhibitors can be useful for the treatment of cocaine induced toxicities, and this discovery is a new use of these agents. Since cocaine induced sensitization is thought to be related to the development of pathophysiological complications ( e.g., seizures, brain ischemia) and cocaine craving in humans abusing cocaine, these drugs and related analogs are considered to be useful for the treatment of cocaine addiction as well.

The following NOS inhibitors may be employed in various chemical forms including pharmaceutically acceptable salts for therapy of cocaine induced toxicity and craving including, but not limited to:

$N^G$-Nitro-L-arginine
$N^G$-Nitro-L-arginine methyl ester
$N^G$-Nitro-L-arginine benzyl ester
$N^G$-Nitro-L-arginine p-nitro-anilide
$N^G$-Monomethyl-L-arginine
7-Nitroindazole The notation "$N^G$" indicates substitution on the nitrogen of the Guanidino group of the arginine.

The NOS inhibitors may be employed in various pharmaceutical forms, including, but not limited to:

solutions for parenteral administration,
tablets and capsules for oral administration,
subcutaneous/dermal implants and patches for slow release.

The above disclosed invention has a number of features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention within the scope of the appended claims.

TABLE 1

Effect of repeated cocaine administration on convulsive response and survival of Swiss-Webster mice pretreated with either saline or L-NAME. Mice received a Single i.p. injection of cocaine (45 mg/kg) each day 60 min after pretreatment with either saline or L-NAME (100 mg/kg). Data is expressed as the total number of animals that seized and survived following the drugs treatment in three separate experiments. Numbers in parentheses indicate percentage.

| | Convulsions | | Survival | |
|---|---|---|---|---|
| Day | Saline/cocaine | L-NAME/cocaine | Saline/cocaine | L-NAME/cocaine |
| 1 | 4/36 (11) | 0/30 (0) | 36/36 (100) | 30/30 (100) |
| 2 | 14/36 (38) | 1/30 (3) | 36/36 (100) | 30/30 (100) |
| 3 | 20/36 (55) | 2/30 (6) | 36/36 (100) | 30/30 (100) |
| 4 | 22/34 (65) | 0/30 (0) | 34/36 (94) | 30/30 (100) |
| 5 | 24/33 (72) | 1/30 (3) | 33/36 (91) | 30/30 (100) |
| 6 | 26/27 (96) | 1/30 (3) | 27/36 (75) | 30/30 (100) |
| 7 | 22/22 (100) | 0/30 (0) | 22/36 (61) | 30/30 (100) |

TABLE 2

Affinity of selected reference drugs for the NMDA receptor labeled with [$^3$H]CGP 39653 and the PCP receptor labeled with [$^3$H]MK-801, relatively to the effect of NOS inhibitors, in mouse cortical membranes.

| Drug | [$^3$H]CGP 39653 Ki (uM) | [$^3$H]MK-801 Ki (uM) |
|---|---|---|
| L-Glutamate | 0.45 ± 0.04 | — |
| D-Aspartate | 0.72 ± 0.06 | — |
| L-Aspartate | 2.10 ± 0.25 | — |
| AP-5 | 2.23 ± 0.18 | — |
| MK-801 | — | 0.003 ± 0.0002 |
| PCP | — | 0.055 ± 0.004 |
| L-NAME | N.E. | N.E. |
| NO-Arg | N.E. | N.E. |

Competition binding assays were carried out using 14 nM [$^3$H]CGP 39653 and 2 nM [$^3$H]MK-801. L-NAME and NO-Arg at a concentration range of 0.01 to 100 uM, each, had no effect (N.E.) on the binding of the two tritium labeled ligands. Data represents the mean ±S.D. of three experiments.

I claim:

1. A method for treating the toxic effects of cocaine in a human subject comprising administering to said subject an effective cocaine induced toxicity reducing amount of a nitric oxide synthase inhibitor for a period of time effective to reduce said cocaine induced toxicity.

2. The method according to claim 1, in which said nitric oxide synthase inhibitor is at least one selected from the group consisting of $N_G$-Nitro-L-arginine, $N^G$-Nitro-L-arginine methyl ester, $N^G$-Nitro-L-arginine benzyl ester, $N^G$-Nitro-L-arginine p-nitro-anilide, $N^G$-Monomethyl-L-arginine, 7-Nitroindazole, and a pharmaceutically acceptable salt thereof.

3. The method according to claim 1, in which said administering is conducted orally, intramuscularly, subcutaneously, transdermally, intravenously, or intraperitoneally.

4. A method for treating the toxic effects of repetitive cocaine administrations on a human subject comprising administering to said subject an effective toxic effects reducing amount of a nitric oxide synthase inhibitor for a period of time sufficient to reduce said toxic effects of repetitive cocaine administrations.

5. The method according to claim 4, in which said nitric oxide synthase inhibitor is at least one selected from the group consisting of $N^G$-Nitro-L- arginine, $N^G$-Nitro-L-arginine methyl ester, $N^G$-Nitro-L-arginine benzyl ester, $N^G$-Nitro-L-arginine p-nitro-anilide, $N^G$-Monomethyl-L-arginine, 7-Nitroindazole, and a pharmaceutically acceptable salt thereof.

6. The method according to claim 4, in which said administering is conducted orally, intramuscularly, subcutaneously, transdermally, intravenously, or intraperitoneally.

* * * * *